United States Patent [19]
Park et al.

[11] Patent Number: 5,583,039
[45] Date of Patent: Dec. 10, 1996

[54] *ESCHERICHIA COLI* CONTAINING A GENE ENCODING A MALTOGENIC AMYLASE BLMA OF *BACILLUS LICHENIFORMIS* AND GENE PRODUCT PRODUCED BY SAME

[75] Inventors: Kwan H. Park, Seoul; In C. Kim, Incheon; Key H. Kim; Jae H. Cha, both of Seoul; So Y. Jang, Pusan; Jeoung R. Kim, Incheon; Byung C. Seo; Yang D. Choi, both of Seoul, all of Rep. of Korea

[73] Assignees: Sunkyong Industries Ltd.; Doosan Technical Center, both of Kyonggi-do; Sunhill Glucose Co., Ltd., Seoul, all of Rep. of Korea

[21] Appl. No.: 152,271

[22] Filed: Nov. 12, 1993

Related U.S. Application Data

[63] Continuation-in-part of Ser. No. 534,679, Jun. 7, 1990, abandoned.

[51] Int. Cl.⁶ ........................................ C12N 1/20
[52] U.S. Cl. .......................... 435/252.33; 435/172.3; 435/202; 435/320.1; 435/836; 536/23.2; 536/23.7; 530/350; 530/825
[58] Field of Search .................. 435/188, 172.3, 435/320.1, 836, 252.33, 252.3, 252.31, 202; 536/23.2, 23.7; 530/350, 825

[56] References Cited

U.S. PATENT DOCUMENTS

| | | | |
|---|---|---|---|
| 4,469,791 | 9/1984 | Colson et al. ........................ | 435/202 |
| 4,493,893 | 1/1985 | Mielenz et al. ...................... | 435/201 |
| 4,598,048 | 7/1986 | Diderichsen et al. ................ | 435/201 |
| 4,642,288 | 2/1987 | De Miguel et al. .................. | 435/202 |
| 4,673,638 | 6/1987 | Grosch et al. ........................ | 435/34 |
| 4,695,546 | 9/1987 | Aiba et al. ............................ | 435/172.3 |

OTHER PUBLICATIONS

Joyet, P. et al., "Cloning of a thermostable α-amylase gene from Bacillus licheniformis and its expression in Escherichia coli and Bacillus subtilis", FEMS Microbiology Letters 21 (1984) 353–358.

Kim, In-Cheol et al., "Catalytic Properties of the Cloned Amylase from Bacillus licheniformis", The Journal of Biological Chemistry, vol. 267, No. 31 Issue of Nov. 5, pp. 22108–22114 (1992).

Skyes Biochemistry 1988 pp. 120–123, Freeman, New York.

*Primary Examiner*—John L. LeGuyader
*Attorney, Agent, or Firm*—Michael L. Dunn

[57] ABSTRACT

An *Escherichia coli* (ATCC 68319) containing a gene encoding a novel maltogenic amylase of *Bacillus licheniformis* (BLMA), wherein said gene has a length of about 3.5 kb; said gene expresses a gene product capable of hydrolyzing cyclodextrin, pullulan, as well as starch at an optimum temperature of about 50° C. at a pH of about 7; said gene product has sugar transferase activity in the presence of glucose; and said *Escherichia coli* produces said gene product optimally when grown in Luria broth, for 24 hours, at 37° C.

2 Claims, 11 Drawing Sheets

```
                TGAGGCTGTTTCTCGACCGGATCGCTTCGCCTCGCCTGACAACCGTGCAACAGCCTGTTGTTGAAA        -226
TGGGAGAGGCTTGCGCGAGAATCCTGCTGAAAAAAATGAATGAAGACGGAGGCGCCGCAACAGATCAATTTTTTT         -151
AACCGGAACTTATTGTCCGCGAATCGACTTTGTAGGGTGTCTCATTCTGTTACCGTTAACAGCTGAAAATGATTG          -76
TTCCTGTTACCGCCGTCATGATAATTTCAGAATAAAAGCCGGTTTATCACAACCGGACAACCAAAAGGGGGAAAC           -1
+1
ATGATCGAATTAGCAGCGATACATCATCAGCCTTTCAACTCTGATGCCTATTCTTACAATGGACGGACATTGCAC           75
MetIleGluLeuAlaAlaIleHisHisGlnProPheAsnSerAspAlaTyrSerTyrAsnGlyArgThrLeuHis            25
+1
ATCAAGATCCGTACAAAAAGGATGATGCCGAACACGTCGCTTGGTTTGGGGCGATCCTTACGAATACACCGGCG           150
IleLysIleArgThrLysLysAspAspAlaGluHisValAlaTrpPheGlyAlaIleLeuThrAsnThrProAla            50
CACATGGAAAGCGAACGAGCTTACGTGGCGAAAATTGGCCGCAACAAGCAGCCCATGATTACTGGTTTGCCGAAG           225
HisMetGluSerGluArgAlaTyrValAlaLysIleGlyArgAsnLysGlnProMetIleThrGlyLeuProLys            75
TGCGGCCTCCATTCAGGCTCAGCAATACGGATTTATCTGACAGCCCTGATGATCGAGACACTTTTTACGGAAGCA           300
CysGlyLeuHisSerGlySerAlaIleArgIleTyrLeuThrAlaLeuMetIleGluThrLeuPheThrGluAla           100
ATGGTGCATGTCCGTTTCCGATATAGGCAAACACATGTTTTAAATTTCCGTTTGTTCATGAGGCAGACACGTTTG           375
MetValHisValArgPheArgTyrArgGlnThrHisValLeuAsnPheArgLeuPheMetArgGlnThrArgLeu           125
ATGCACCGACTGGGTCAAATCAACCGTCTGGTATCAAATTTTTCCGGAGCTTTCCGAGCGGGCGGGAAGATTTGC           450
MetHisArgLeuGlyGlnIleAsnArgLeuValSerAsnPheSerGlyAlaPheArgAlaGlyGlyLysIleCys           150
TCCGGAAAACCTTTGCCATGGGGAAGGAAAGATCCTGAGGCGCACGATTTTTTCGGAGGGCATTTGCAGGGGATC           525
SerGlyLysProLeuProTrpGlyArgLysAspProGluAlaHisAspPhePheGlyGlyHisLeuGlnGlyIle           175
ATGACAAGCTGGACTATTTGGAAGACTTGGGGGGAGGCCGGAATCTATTTGACGCCGATCTTTGCCGCGCCTTCC           600
MetThrSerTrpThrIleTrpLysThrTrpGlyGluAlaGlyIleTyrLeuThrProIlePheAlaAlaProSer           200
AACCATAAATACGACACATTGGACTATTGCTCCATCGATCCGCATTTTGGCGATGAGGAGCTCTTTCGCACCGTG           675
AsnHisLysTyrAspThrLeuAspTyrCysSerIleAspProHisPheGlyAspGluGluLeuPheArgThrVal           225
GTCAGCCGGATTCACGAGCGGGGAATGAAAATCATG CTTGATGCTGTTTTTAACCAC ATTGGCACGTCGCAAGAG          750
ValSerArgIleHisGluArgGlyMetLysIleMet LeuAspAlaValPheAsnHis  IleGlyThrSerGlnGlu         250
TGGCAGGATGTTGTCAAAAACGGGGAAACGTCCCGCTATAAAGACTGGTTCATATTCATTCTTTCCCTGTTAAAG           825
TrpGlnAspValValLysAsnGlyGluThrSerArgTyrLysAspTrpPheIlePheIleLeuSerLeuLeuLys           275
AAGGCAGCTATGATACATTTGCGTTTAGTCCCGAGATGCCGAAGCTCAATAGCCGGAACCCGGAAGTTCAGGCTT           900
LysAlaAlaMetIleHisLeuArgLeuValProArgCysArgSerSerIleAlaGlyThrArgLysPheArgLeu           300
ATTTGCTTGATATTGCGCTGTACTGGATCCGCGAATTTGATATCGACGGCT GGCGTTTGGATGTGGCAAATGAAG          975
IleCysLeuIleLeuArgCysThrGlySerAlaAsnLeuIleSerThrAla GlyValTrpMetTrpGlnMetLys          325
TTG ATCATGCGTTTTGGAAGAAATTCCGGCAAGCCGTCACCGGAAAAGCCCGACATTTTTATATTGGGC GAAATC         1050
Leu IleMetArgPheGlyArgAsnSerGlyLysProSerProGluLysProAspIlePheIleLeuGly  GluIle         350
TGGCAT CAGGCTGATCCGTGGCTTAGAGGAGACGAATTTCATATCGGTCATGAACTACCCGTTCACAGAACCGAT        1125
TrpHis GlnAlaAspProTrpLeuArgGlyAspGluPheHisIleGlyHisGluLeuProValHisArgThrAsp          375
GATTCACTATTTTTCAGACGGATCGATTTCAGCTCGCAAATAGCCAGCCGCATCAATTCGCAAAAAATGAGCGGG         1200
AspSerLeuPhePheArgArgIleAspPheSerSerGlnIleAlaSerArgIleAsnSerGlnLysMetSerGly           400
ATGAAGCAGGTGAAGGAGGTGATGTTGAAT TTGCTGGACAGTCACGAG CGGATTTTGACAAGATGCGGAGGAGAT        1275
MetLysGlnValLysGluValMetLeuAsn LeuLeuAspSerHisGlu ArgIleLeuThrArgCysGlyGlyAsp          425
CAGAGAAAAGGTGCGCGTCTCTTTTGGCATTCATGTTTGCTCAGACAGGGTCGCATTTATTACCCACGGAAGTCG         1350
GlnArgLysGlyAlaArgLeuPheTrpHisSerCysLeuLeuArgGlnGlyArgIleTyrTyrProArgLysSer           450
GGCTTCACGGCGGCGATGATCCATTGTGCCGGAAGTGCATGGTTTGGGAAGAGGAAAAACAGAATCAAGAGATGC         1425
GlyPheThrAlaAlaMetIleHisCysAlaGlySerAlaTrpPheGlyLysArgLysAsnArgIleLysArgCys           475
CTCGCATTTATGAAACCCCTGATCGCTTTGCGAAAACAAGAGAATGATGTATTGACTTATGGCGCGCTTGAGTGG         1500
LeuAlaPheMetLysProLeuIleAlaLeuArgLysGlnGluAsnAspValLeuThrTyrGlyAlaLeuGluTrp           500
AAGCTGGTTGATGACCAAAACGATTTTGTCAGTTTTTCTCGAACGCATGAAGGAAAAGAGCTGATCTACTTCTTC         1575
LysLeuValAspAspGlnAsnAspPheValSerPheSerArgThrHisGluGlyLysGluLeuIleTyrPhePhe           525
CACCAGGGCAGAGAGGTGCGCCGTGTCAGATTGCGGGATTTGAAGATTGCAAGCGATAAAAGAATATACGATGCG         1650
HisGlnGlyArgGluValArgArgValArgLeuArgAspLeuLysIleAlaSerAspLysArgIleTyrAspAla           550
TGGACGGAAGAAGCGCTTCACGATGATGATGTGGTCGACATTCAGCCAGGCGATTTTTCATTTTTGGGGCGGTCT         1725
TrpThrGluGluAlaLeuHisAspAspAspValValAspIleGlnProGlyAspPheSerPheLeuGlyArgSer           575
AAATTCTGTTAGGCCTAACAGGTTTAAAACTATTGTAAGCGTTTCTGTCGAGGATTACAATTGTCTCAGATTCCA         1800
LysPheCys***                                                                         578
AGATAGAAGGGGGAAAAAAGATGCAACATTTAAAAAAAGGAATTTTAGTGCTGCTGGCGTCAGTTCTGCTGTTCG         1875
GTGTTCCCGCGCTGTTCAAGTTCAAAGGAAACGGGAGGGCAGCGCGCGGGAAAAAAGTTTTTTGACCGTGTCTGTA         1950
GAAGAGGTCTATAAACCTTACCGTCGAAAGCATAAAGGAAGGTTTTGAAAAAGAGAACGAGGGACAGTCAAAATC         2025
CATTGAAAAGCCGATGTTCGACCACGTTGAAGACCTTCCGTTGACGGTACCGGCAGCAATGCGACCCGATGTCCA         2100
TGCTTGCGCCATACGACCGTATCGCGGCTTAGGACAGCAAGGTCATTTGCAGATAGTCAAACCGTCTGACACAAAA         2175
AGCTT                                                                              2180
```

FIG 2

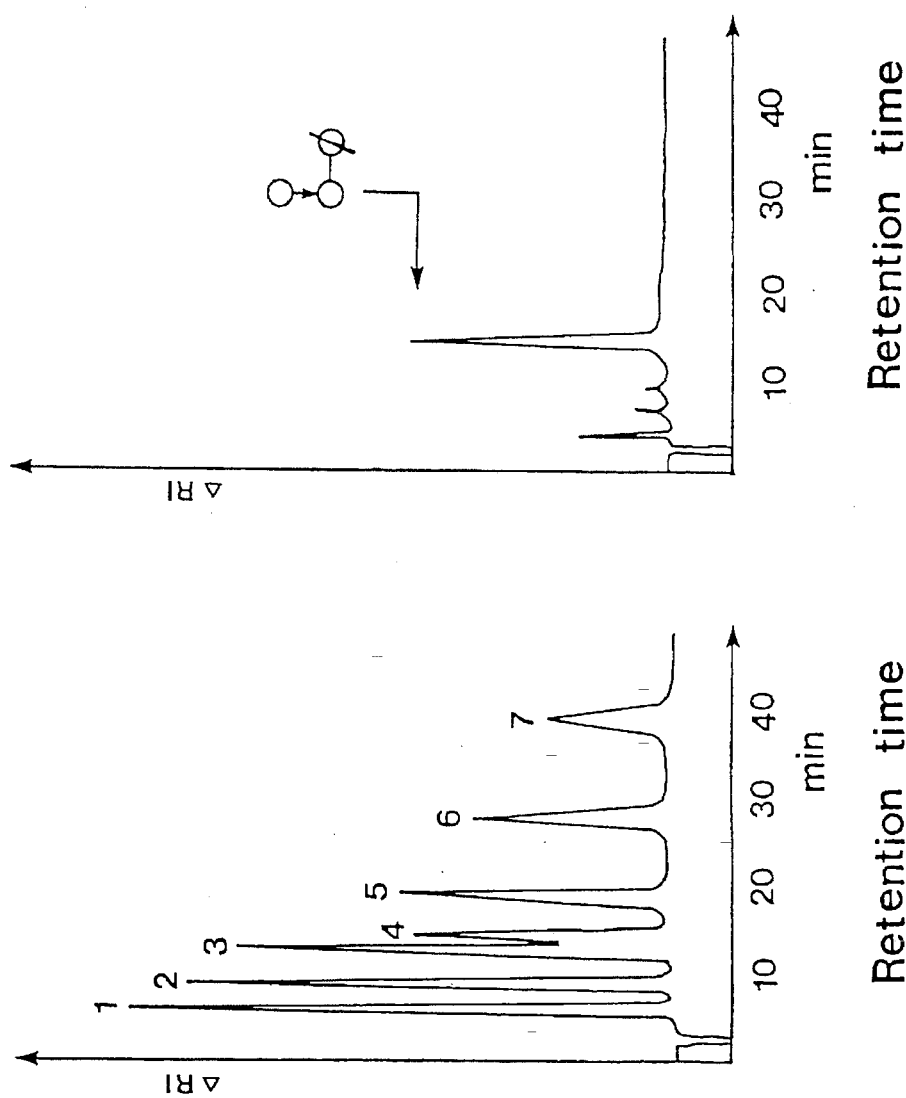

IP  P  H

SEQUENCE LISTING ( 1 ) GENERAL INFORMATION:

( i i i ) NUMBER OF SEQUENCES: 1

( 2 ) INFORMATION FOR SEQ ID NO: 1 :

( i ) SEQUENCE CHARACTERISTICS:
        ( A ) LENGTH: 2471 nucleotides
        ( B ) TYPE: Nucleic acids
        ( C ) STRANDEDNESS: double stranded
        ( D ) TOPOLOGY: circular ( i i ) MOLECULE TYPE: Genomic DNA
   ( A ) DESCRIPTION: The nucleotide sequence of 2471 bp DNA fragment of B. licheniformis containing an open reading frame capable of encoding a maltogenic amylase, its 5'and 3' sequences, and 578 amino acid deduced sequence of the open reading frame.

( i i i ) HYPOTHETICAL: No ( i v ) ANTI-SENSE: No ( v ) FRAGMENT TYPE: contains N-, C-, and internal fragments.

( v i ) ORIGINAL SOURCE:
   ( A ) ORGANISM: Gram positive Bacterium
   ( B ) STRAIN: Bacillus licheniformis
   ( C ) INDIVIDUAL ISOLATE: ATCC 27811
   ( D ) DEVELOPMENTAL STAGE: vegetative cells ( v i i ) IMMEDIATE SOURCE:
   ( B ) CLONE: pIJ322

( i x ) FEATURE:
   ( A ) NAME/KEY: B. licheniformis Maltogenic Amylase
   ( B ) LOCATION: putative promoter; 197- 202 (-35), 235-240 (-10)
       putative ribosome binding site; 282-287
       putative translation initiation site; 292
       translation termination site; 2026
   ( C ) IDENTIFICATION METHOD: by similarity with known sequence or to an established consensus sequence
   ( D ) OTHER INFORMATION: The E. coli transformants harboring the clone containing the sequence showed starch hydrolyzing phenotype on a starch agar plate only after the cell membrane was disrupted with D-cycloserine. The gene product hydrolyzes starch, pullulan, and cyclodextrin and has transferase activity.

( x ) PUBLICATION INFORMATION:
   ( A ) AUTHORS: KIM, IN CHEOL
       CHA, JAE HO
       KIM, JEOUNG RYUL
       JANG, SO YAOUNG
       SEO, BYUNG CHEOL
       CHEONG, TAE KYOU
       LEE, DAE SIL
       CHOI, YANG DO
       PARK, KWAN HWA
   ( B ) TITLE: CATALYTIC PROPERTIES OF THE CLONED AMYLASE FROM BACILLUS licheniformis.
   ( C ) JOURNAL: THE JOURNAL OF BIOLOGICAL CHEMISTRY
   ( D ) VOLUME: 267
   ( E ) ISSUE: NO. 31
   ( F ) PAGES: 22108-22114
   ( G ) DATE: 05-NOV-1992
   ( K ) RELEVANT RESIDUES IN SEQ ID NO: 1 : from 1 bp to 2471

( x i ) SEQUENCE DESCRIPTION: SEQ ID NO: 1: The nucleotide sequence of 2471 bp DNA fragment of B. licheniformis containing an open reading frame capable of encoding a maltogenic amylase, its 5' and 3' sequence, and deduced 578 amino acid deduced sequence of the open reading frame.

```
TGAGGCTGTT  TCTCGACCGG  ATCGCTTCGC  CTCGCCTGAC  AACCGTGCAA  CAGCCTGTTG         60

TTGAAATGGG  AGAGGCTTGC  GCGAGAATCC  TGCTGAAAAA  AATGAATGAA  GACGGAGGCG        120

CCGCAACAGA  TCAATTTTTT  TAACCGGAAC  TTATTGTCCG  CGAATCGACT  TTGTAGGGTG        180

TCTCATTCTG  TTACCGTTAA  CAGCTGAAAA  TGATTGTTCC  TGTTACCGCC  GTCATGATAA        240

TTTCAGAATA  AAAGCCGGTT  TATCACAACC  GGACAACCAA  AAGGGGGAAA  C   ATG  ATC      297
                                                              Met  Ile
                                                               1

GAA  TTA  GCA  GCG  ATA  CAT  CAT  CAG  CCT  TTC  AAC  TCT  GAT  GCC  TAT  TCT    345
Glu  Leu  Ala  Ala  Ile  His  His  Gln  Pro  Phe  Asn  Ser  Asp  Ala  Tyr  Ser
      5              10                          15
```

| | | | | | | | | | | | | | | | | |
|---|---|---|---|---|---|---|---|---|---|---|---|---|---|---|---|---|
| TAC | AAT | GGA | CGG | ACA | TTG | CAC | ATC | AAG | ATC | CGT | ACA | AAA | AAG | GAT | GAT | 393 |
| Tyr | Asn | Gly | Arg | Thr | Leu | His | Ile | Lys | Ile | Arg | Thr | Lys | Lys | Asp | Asp | |
| | 20 | | | | 25 | | | | | 30 | | | | | | |
| GCC | GAA | CAC | GTC | GCT | TGG | TTT | GGG | GCG | ATC | CTT | ACG | AAT | ACA | CCG | GCG | 441 |
| Ala | Glu | His | Val | Ala | Trp | Phe | Gly | Ala | Ile | Leu | Thr | Asn | Thr | Pro | Ala | |
| 35 | | | | | 40 | | | | | 45 | | | | | 50 | |
| CAC | ATG | GAA | AGC | GAA | CGA | GCT | TAC | GTG | GCG | AAA | ATT | GGC | CGC | AAC | AAG | 489 |
| His | Met | Glu | Ser | Glu | Arg | Ala | Tyr | Val | Ala | Lys | Ile | Gly | Arg | Asn | Lys | |
| | | | | 55 | | | | | 60 | | | | | 65 | | |
| CAG | CCC | ATG | ATT | ACT | GGT | TTG | CCG | AAG | TGC | GGC | CTC | CAT | TCA | GGC | TCA | 537 |
| Gln | Pro | Met | Ile | Thr | Gly | Leu | Pro | Lys | Cys | Gly | Leu | His | Ser | Gly | Ser | |
| | | | 70 | | | | | 75 | | | | | 80 | | | |
| GCA | ATA | CGG | ATT | TAT | CTG | ACA | GCC | CTG | ATG | ATC | GAG | ACA | CTT | TTT | ACG | 585 |
| Ala | Ile | Arg | Ile | Tyr | Leu | Thr | Ala | Leu | Met | Ile | Glu | Thr | Leu | Phe | Thr | |
| | | 85 | | | | | 90 | | | | | 95 | | | | |
| GAA | GCA | ATG | GTG | CAT | GTC | CGT | TTC | CGA | TAT | AGG | CAA | ACA | CAT | GTT | TTA | 633 |
| Glu | Ala | Met | Val | His | Val | Arg | Phe | Arg | Tyr | Arg | Gln | Thr | His | Val | Leu | |
| | | 100 | | | | | 105 | | | | | 110 | | | | |
| AAT | TTC | CGT | TTG | TTC | ATG | AGG | CAG | ACA | CGT | TTG | ATG | CAC | CGA | CTG | GGT | 681 |
| Asn | Phe | Arg | Leu | Phe | Met | Arg | Gln | Thr | Arg | Leu | Met | His | Arg | Leu | Gly | |
| 115 | | | | | 120 | | | | | 125 | | | | | 130 | |
| CAA | ATC | AAC | CGT | CTG | GTA | TCA | AAT | TTT | TCC | GGA | GCT | TTC | CGA | GCG | GGC | 729 |
| Gln | Ile | Asn | Arg | Leu | Val | Ser | Asn | Phe | Ser | Gly | Ala | Phe | Arg | Ala | Gly | |
| | | | | 135 | | | | | 140 | | | | | 145 | | |
| GGG | AAG | ATT | TGC | TCC | GGA | AAA | CCT | TTG | CCA | TGG | GGA | AGG | AAA | GAT | CCT | 777 |
| Gly | Lys | Ile | Cys | Ser | Gly | Lys | Pro | Leu | Pro | Trp | Gly | Arg | Lys | Asp | Pro | |
| | | | 150 | | | | | 155 | | | | | 160 | | | |
| GAG | GCG | CAC | GAT | TTT | TTC | GGA | GGG | CAT | TTG | CAG | GGG | ATC | ATG | ACA | AGC | 825 |
| Glu | Ala | His | Asp | Phe | Phe | Gly | Gly | His | Leu | Gln | Gly | Ile | Met | Thr | Ser | |
| | | 165 | | | | | 170 | | | | | 175 | | | | |
| TGG | ACT | ATT | TGG | AAG | ACT | TGG | GGG | GAG | GCC | GGA | ATC | TAT | TTG | ACG | CCG | 873 |
| Trp | Thr | Ile | Trp | Lys | Thr | Trp | Gly | Glu | Ala | Gly | Ile | Tyr | Leu | Thr | Pro | |
| | 180 | | | | | 185 | | | | | 190 | | | | | |
| ATC | TTT | GCC | GCG | CCT | TCC | AAC | CAT | AAA | TAC | GAC | ACA | TTG | GAC | TAT | TGC | 921 |
| Ile | Phe | Ala | Ala | Pro | Ser | Asn | His | Lys | Tyr | Asp | Thr | Leu | Asp | Tyr | Cys | |
| 195 | | | | | 200 | | | | | 205 | | | | | 210 | |
| TCC | ATC | GAT | CCG | CAT | TTT | GGC | GAT | GAG | GAG | CTC | TTT | CGC | ACC | GTG | GTC | 969 |
| Ser | Ile | Asp | Pro | His | Phe | Gly | Asp | Glu | Glu | Leu | Phe | Arg | Thr | Val | Val | |
| | | | | 215 | | | | | 220 | | | | | 225 | | |
| AGC | CGG | ATT | CAC | GAG | CGG | GGA | ATG | AAA | ATC | ATG | CTT | GAT | GCT | GTT | TTT | 1017 |
| Ser | Arg | Ile | His | Glu | Arg | Gly | Met | Lys | Ile | Met | Leu | Asp | Ala | Val | Phe | |
| | | | 230 | | | | | 235 | | | | | 240 | | | |
| AAC | CAC | ATT | GGC | ACG | TCG | CAA | GAG | TGG | CAG | GAT | GTT | GTC | AAA | AAC | GGG | 1065 |
| Asn | His | Ile | Gly | Thr | Ser | Gln | Glu | Trp | Gln | Asp | Val | Val | Lys | Asn | Gly | |
| | | 245 | | | | | 250 | | | | | 255 | | | | |
| GAA | ACG | TCC | CGC | TAT | AAA | GAC | TGG | TTC | ATA | TTC | ATT | CTT | TCC | CTG | TTA | 1113 |
| Glu | Thr | Ser | Arg | Tyr | Lys | Asp | Trp | Phe | Ile | Phe | Ile | Leu | Ser | Leu | Leu | |
| | 260 | | | | | 265 | | | | | 270 | | | | | |
| AAG | AAG | GCA | GCT | ATG | ATA | CAT | TTG | CGT | TTA | GTC | CCG | AGA | TGC | CGA | AGC | 1161 |
| Lys | Lys | Ala | Ala | Met | Ile | His | Leu | Arg | Leu | Val | Pro | Arg | Cys | Arg | Ser | |
| 275 | | | | | 280 | | | | | 285 | | | | | 290 | |
| TCA | ATA | GCC | GGA | ACC | CGG | AAG | TTC | AGG | CTT | ATT | TGC | TTG | ATA | TTG | CGC | 1209 |
| Ser | Ile | Ala | Gly | Thr | Arg | Lys | Phe | Arg | Leu | Ile | Cys | Leu | Ile | Leu | Arg | |
| | | | | 295 | | | | | 300 | | | | | 305 | | |
| TGT | ACT | GGA | TCC | GCG | AAT | TTG | ATA | TCG | ACG | GCT | GGC | GTT | TGG | ATG | TGG | 1257 |
| Cys | Thr | Gly | Ser | Ala | Asn | Leu | Ile | Ser | Thr | Ala | Gly | Val | Trp | Met | Trp | |
| | | | 310 | | | | | 315 | | | | | 320 | | | |
| CAA | ATG | AAG | TTG | ATC | ATG | CGT | TTT | GGA | AGA | AAT | TCC | GGC | AAG | CCG | TCA | 1305 |
| Gln | Met | Lys | Leu | Ile | Met | Arg | Phe | Gly | Arg | Asn | Ser | Gly | Lys | Pro | Ser | |
| | | 325 | | | | | 330 | | | | | 335 | | | | |

| | | | | | | | | | | | | | | | | |
|---|---|---|---|---|---|---|---|---|---|---|---|---|---|---|---|---|
| CCG | GAA | AAG | CCC | GAC | ATT | TTT | ATA | TTG | GGC | GAA | ATC | TGG | CAT | CAG | GCT | 1353 |
| Pro | Glu | Lys | Pro | Asp | Ile | Phe | Ile | Leu | Gly | Glu | Ile | Trp | His | Gln | Ala | |
| | 340 | | | | 345 | | | | | 350 | | | | | | |
| GAT | CCG | TGG | CTT | AGA | GGA | GAC | GAA | TTT | CAT | ATC | GGT | CAT | GAA | CTA | CCC | 1401 |
| Asp | Pro | Trp | Leu | Arg | Gly | Asp | Glu | Phe | His | Ile | Gly | His | Glu | Leu | Pro | |
| 355 | | | | 360 | | | | | 365 | | | | | | 370 | |
| GTT | CAC | AGA | ACC | GAT | GAT | TCA | CTA | TTT | TTC | AGA | CGG | ATC | GAT | TTC | AGC | 1449 |
| Val | His | Arg | Thr | Asp | Asp | Ser | Leu | Phe | Phe | Arg | Arg | Ile | Asp | Phe | Ser | |
| | | | | 375 | | | | | 380 | | | | | 385 | | |
| TCG | CAA | ATA | GCC | AGC | CGC | ATC | AAT | TCG | CAA | AAA | ATG | AGC | GGG | ATG | AAG | 1497 |
| Ser | Gln | Ile | Ala | Ser | Arg | Ile | Asn | Ser | Gln | Lys | Met | Ser | Gly | Met | Lys | |
| | | | 390 | | | | | 395 | | | | | 400 | | | |
| CAG | GTG | AAG | GAG | GTG | ATG | TTG | AAT | TTG | CTG | GAC | AGT | CAC | GAG | CGG | ATT | 1545 |
| Gln | Val | Lys | Glu | Val | Met | Leu | Asn | Leu | Leu | Asp | Ser | His | Glu | Arg | Ile | |
| | | 405 | | | | | 410 | | | | | 415 | | | | |
| TTG | ACA | AGA | TGC | GGA | GGA | GAT | CAG | AGA | AAA | GGT | GCG | CGT | CTC | TTT | TGG | 1593 |
| Leu | Thr | Arg | Cys | Gly | Gly | Asp | Gln | Arg | Lys | Gly | Ala | Arg | Leu | Phe | Trp | |
| | 420 | | | | | 425 | | | | | 430 | | | | | |
| CAT | TCA | TGT | TTG | CTC | AGA | CAG | GGT | CGC | ATT | TAT | TAC | CCA | CGG | AAG | TCG | 1641 |
| His | Ser | Cys | Leu | Leu | Arg | Gln | Gly | Arg | Ile | Tyr | Tyr | Pro | Arg | Lys | Ser | |
| 435 | | | | | 440 | | | | | 445 | | | | | 450 | |
| GGC | TTC | ACG | GCG | GCG | ATG | ATC | CAT | TGT | GCC | GGA | AGT | GCA | TGG | TTT | GGG | 1689 |
| Gly | Phe | Thr | Ala | Ala | Met | Ile | His | Cys | Ala | Gly | Ser | Ala | Trp | Phe | Gly | |
| | | | | 455 | | | | | 460 | | | | | 465 | | |
| AAG | AGG | AAA | AAC | AGA | ATC | AAG | AGA | TGC | CTC | GCA | TTT | ATG | AAA | CCC | CTG | 1737 |
| Lys | Arg | Lys | Asn | Arg | Ile | Lys | Arg | Cys | Leu | Ala | Phe | Met | Lys | Pro | Leu | |
| | | | 470 | | | | | 475 | | | | | 480 | | | |
| ATC | GCT | TTG | CGA | AAA | CAA | GAG | AAT | GAT | GTA | TTG | ACT | TAT | GGC | GCG | CTT | 1785 |
| Ile | Ala | Leu | Arg | Lys | Gln | Glu | Asn | Asp | Val | Leu | Thr | Tyr | Gly | Ala | Leu | |
| | | 485 | | | | | 490 | | | | | 495 | | | | |
| GAG | TGG | AAG | CTG | GTT | GAT | GAC | CAA | AAC | GAT | TTT | GTC | AGT | TTT | TCT | CGA | 1833 |
| Glu | Trp | Lys | Leu | Val | Asp | Asp | Gln | Asn | Asp | Phe | Val | Ser | Phe | Ser | Arg | |
| | 500 | | | | | 505 | | | | | 510 | | | | | |
| ACG | CAT | GAA | GGA | AAA | GAG | CTG | ATC | TAC | TTC | TTC | CAC | CAG | GGC | AGA | GAG | 1881 |
| Thr | His | Glu | Gly | Lys | Glu | Leu | Ile | Tyr | Phe | Phe | His | Gln | Gly | Arg | Glu | |
| 515 | | | | | 520 | | | | | 525 | | | | | 530 | |
| GTG | CGC | CGT | GTC | AGA | TTG | CGG | GAT | TTG | AAG | ATT | GCA | AGC | GAT | AAA | AGA | 1929 |
| Val | Arg | Arg | Val | Arg | Leu | Arg | Asp | Leu | Lys | Ile | Ala | Ser | Asp | Lys | Arg | |
| | | | | 535 | | | | | 540 | | | | | 545 | | |
| ATA | TAC | GAT | GCG | TGG | ACG | GAA | GAA | GCG | CTT | CAC | GAT | GAT | GAT | GTG | GTC | 1977 |
| Ile | Tyr | Asp | Ala | Trp | Thr | Glu | Glu | Ala | Leu | His | Asp | Asp | Asp | Val | Val | |
| | | | 550 | | | | | 555 | | | | | 560 | | | |
| GAC | ATT | CAG | CCA | GGC | GAT | TTT | TCA | TTT | TTG | GGG | CGG | TCT | AAA | TTC | TGT | 2025 |
| Asp | Ile | Gln | Pro | Gly | Asp | Phe | Ser | Phe | Leu | Gly | Arg | Ser | Lys | Phe | Cys | |
| | | 565 | | | | | 570 | | | | | 575 | | | | |
| TAG | | | | | | | | | | | | | | | | |
| *** | GCCTAACAGG | TTTAAAACTA | TTGTAAGCGT | TTCTGTCGAG | GATTACAATT | | | | | | | | | | | 2078 |

GTCTCAGATT CCAAGATAGA AGGGGGAAAA AAGATGCAAC ATTTAAAAAA AGGAATTTTA 2138
GTGCTGCTGG CGTCAGTTCT GCTGTTCGGT GTTCCCGCGC TGTTCAAGTT CAAAGGAAAC 2198
GGGAGGGCAG CGGCGGGAAA AAAGTTTTTT GACCGTGTCT GTAGAAGAGG TCTATAAACC 2258
TTACCGTCGA AAGCATAAAG GAAGGTTTTG AAAAAGAGAA CGAGGACAG TCAAAATCCA 2318
TTGAAAAGCC GATGTTCGAC CACGTTGAAG ACCTTCCGTT GACGGTACCG GCAGCAATGC 2378
GACCCGATGT CCATGCTTGC GCATACGACC GTATCGCGGC TTAGGACAGC AAGGTCATTT 2438
GCAGATAGTC AAACCGTCTG ACACAAAAAG CTT 2471

ESCHERICHIA COLI CONTAINING A GENE ENCODING A MALTOGENIC AMYLASE BLMA OF BACILLUS LICHENIFORMIS AND GENE PRODUCT PRODUCED BY SAME

This application is a continuation-in-part of U.S. patent application Ser. No. 07/534,679, filed Jun. 7, 1990, now abandoned.

TECHNICAL FIELD

The present invention relates generally to amylolytic enzymes. More particularly, the present invention relates to an *Escherichia coli* containing a gene encoding a novel maltogenic amylase of *Bacillus licheniformis* and the gene product of same.

BACKGROUND OF THE INVENTION

α-Amylase is one of the known enzymes which hydrolyzes α-1,4-linkage of starch producing a mixture of oligosaccharides. In recent years, evidence has mounted in support of the unusual action of amylases which exhibit transferring as well as hydrolyzing activity. New amylases have also been discovered from various microorganisms including maltose forming-, pullulan and/or cyclodextrin hydrolyzing-, and glucose-transferring amylases. α-Amylases from *Thermoactinomyces vulgaris* R-47 (Shimizu et al., *Agric. Biol. Chem.*, 42, 1681 (1978); Sakano et al., *Agric. Biol. Chem.* 46, 1121 (1982) (I)) and *Bacillus stearothermophilis* KP 1064 (Suzuki et al., *Appl. Microbiol. Biotechnol.*, 21, 20 (1985) (I) degrade soluble starch, yielding maltose and glucose as major products. They also hydrolyze cyclodextrins. These unusual enzymes convert pullulan to panose. A new type of pullulanase which produces panose from pullulan was also found in *Bacillis stearothermophilis* (Kuriki et al., *J. Bacterial.*, 170, 1554 (1988) (I); Imanaka et al., *J. Bacteriol.* 171, 369 (1989)), and a gene for the enzyme was cloned and expressed in *Bacillis subtilis*. Suzuki et al. (*Starch* 39, 211 (II) isolated extracellular α-amylase II from *Bacillus thermoamyloliquefaciens* KP1071, which split α-1,6-linkages in amylopectin as well. This enzyme hydrolyzed α- and β-cyclodextrins, and pullulans as well. David et al. (*Starch* 39, 436 (1987)) cloned a gene encoding the amylolytic enzyme of *Bacillus megaterium*. Based on the action pattern of the enzyme, it has been proposed that this enzyme hydrolyzed pullulan as well as starch. Interestingly, it also exhibited glucose transferring activity with the formation of α-1,4-linkage. With the discovery of these new amylases, the scheme of transferring activities on the starch metabolism in the microorganisms was to be elucidated and the production of maltooligosaccharides in large quantities became easier.

Applicants have cloned a gene encoding a new type of amylolytic enzyme, *Bacillus licheniformis* maltogenic amylase, hereinafter referred to as BLMA. The enzyme has the ability to hydrolyze pullulan and cyclodextrin as well as starch. It degrades soluble starch by cleaving maltose units preferentially. The usual thermostable amylase, BLTA, of *Bacillus licheniformis* produces mostly maltoheptaose from starch but cannot hydrolyze pullulan and cyclodextrins (Kim, I. C. Ph.D. thesis, Seoul National University Press, Seoul, Korea (1991)). The BLMA of the present invention also showed the catalytic properties of a new type of α-amylase which exhibited transferring activity with the formation of α-1,6-linkage, which is useful in production of branched oligosaccharide.

Finally, the *Escherichia coli* containing the gene encoding the novel amylolytic enzyme of the present invention was deposited at the ATCC (American Type Culture Collection, 12301 Parklawn Drive, Rockville, Md. 20852, USA) on May 7, 1990 and received ATCC Number 68319.

SUMMARY OF THE PRESENT INVENTION

With the foregoing in mind, it is an object of the present invention to provide an *Escherichia coli* (ATCC 68319) containing a gene encoding a novel amylolytic enzyme of *Bacillus licheniformis*.

It is another object of the present invention to provide a novel amylolytic enzyme of *Bacillus licheniformis* which has the ability to hydrolyze cyclodextrin, pullulan, as well as starch.

It is yet another object of the present invention to provide a novel amylolytic enzyme of *Bacillus licheniformis* which has sugar transferase activity in the presence of glucose.

A further object of the present invention is to provide a novel amylolytic enzyme of *Bacillus licheniformis* which degrades soluble starch by cleaving maltose units preferentially.

Yet another object of the present invention is to provide the gene product produced by said *Escherichia coli*.

These and other objects of the present invention may be achieved by producing an *Escherichia coli* (ATCC 68319) containing a gene encoding a novel amylolytic enzyme of *Bacillus licheniformis* (BLMA), wherein said gene has a length of about 3.5 kb; said gene expresses a gene product capable of hydrolyzing cyclodextrin, pullulan, as well as starch at an optimum temperature of about 50° C. at a pH of about 7; said gene product has sugar transferase activity in the presence of glucose; and said *Escherichia coli* produces said gene product optimally when grown in Luria broth, for 24 hours, at 37° C.

To the accomplishment of the foregoing and related ends, the invention, then, comprises the features hereinafter described and particularly pointed out in the claims, the following description and annexed drawings setting forth in detail a certain illustrative embodiment of the invention, this being indicative, however, of but one preferred embodiment of the invention.

BRIEF DESCRIPTION OF THE DRAWINGS

For a better understanding of the invention as well as other objects and further features thereof, reference is made to the following detailed description to be read in conjunction with the accompanying drawings, wherein:

FIG. 2.—Nucleotide and deduced amino acid sequence of the BLMA gene. The nucleotide sequence was numbered as +1 from the first nucleotide for translation initiation. A putative promoter (−35 and −10 region) and a probable Shine-Dalgarno sequence are underlined. The inverted repeat sequence upstream and downstream of coding region are shown as shaded. Four blocks of conserved sequences among amylases are shown in boxes.

FIGS. 5A and 5B.—High performance liquid chromatographic analysis of the hydrolysis product of pullulan with BLMA. FIG. 5A, chromatogram of standard solution containing glucose (1), maltose (2), maltotriose (3), panose (4), maltotetraose (5), maltopentaose (6), maltohexaose (7). FIG. 5B, chromatogram of reaction product of pullulan with BLMA. The HPLC analysis was carried out under the following conditions: column, Machinery & Nagel Nucleosil 10NH$_2$ (4.6×300 mm); detector, Pye Unicam PU4023 refractive index detector; solvent, acetonitrile/water (65:35, v/v); flow rate, 1.0 ml/min; sample loop, 20 μl.

DETAILED DESCRIPTION AND PREFERRED EMBODIMENT OF THE INVENTIONS

Figure 1A:
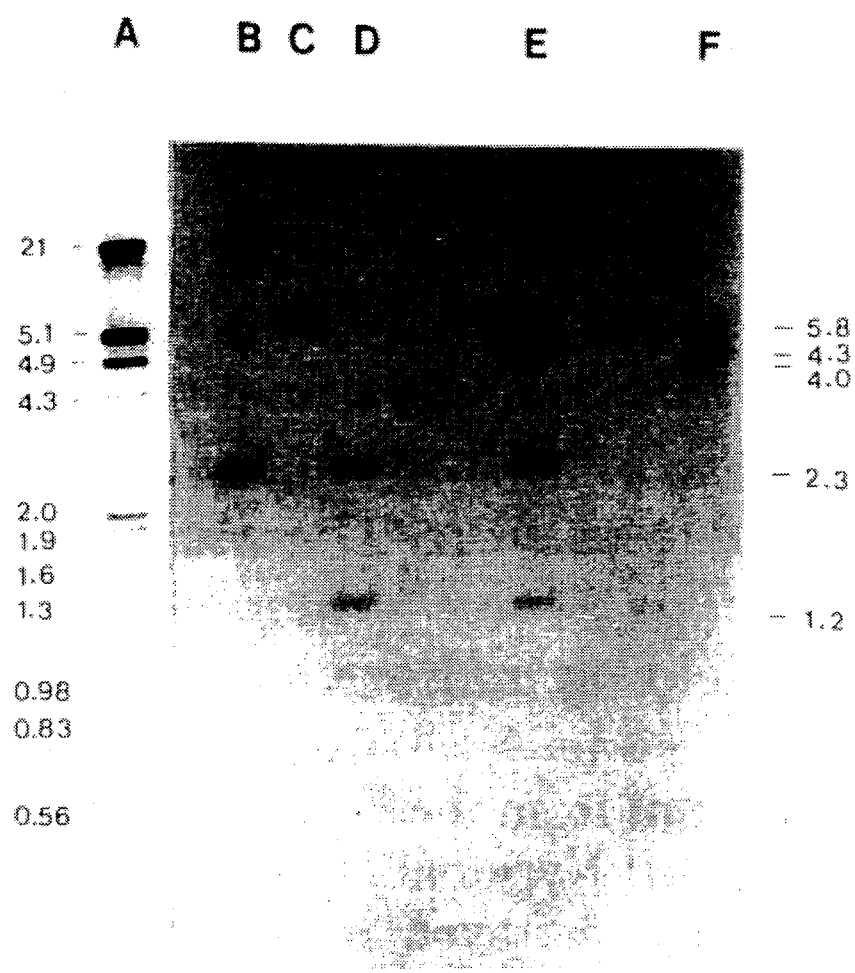
FIG. 1A.—Southern Blot analysis of the genomic DNA of *Bacillus licheniformis*. The genomic DNA of *B. licheniformis* was digested with the restriction enzyme indicated, separated by 0.5% agarose gel electrophoresis, and was transferred onto a nitrocellulose filter. It was hybridyzed with pIJ322 which was labeled with [α-$^{32}$P]dATP by nick translation. Lane A, EcoRI and HindIII-digested phage DNA. Lanes B and C: BamHI- and EcoRI-digested genomic DNA, respectively. Lane D, BamHI and EcoRI double-digested genomic DNA. Lane E, BamHI and EcoRI double-digested pIJ322. Lane F, EcoRI-digested pBR322.

Structures of the carbohydrates and oligosaccharides are defined: pullulan, (-4Glcpαl-6Glcpαl-4Glcpαl-)$_n$; panose, Glcpαl-6Glcpαl-4Glc; isopanose, Glcpαl-4Glcpαl-6Glc; maltotriose, Glcpαl-4Glcpαl-4Glc.

Abbreviations used herein are as follows: BLMA, maltogenic amylase of *Bacillus licheniformis;* BLTA, thermostable α-amylase of *Bacillus licheniformis;* HPLC, high performance liquid chromatography; SDS-PAGE, sodium dodecyl sulfate-polyacrylamide gel electrophoresis; TLC, thin layer chromatography; NMR, nuclear magnetic resonance; bp, base pair; kbp, kilobase pairs; LB, Luria broth.

EXPERIMENTAL PROCEDURES

Materials and Bacterial Strains—Maltooligosaccharides, α-, β-, γ- cyclodextrin, and panose were purchased from Sigma Chemical Co. CST. Louise, U.S.A.). Isopanose was a gift from Dr. Y. Sakano, Tokyo Noko University, Japan. *Bacillus licheniformis* ATCC 27811 was obtained from the American Type Culture Collection (ATCC) and used as the donor strain for the BLMA gene. *Escherichia coli* HB 101 was used as the host strain for recombinant DNA.

Cloning and Characterization of BLMA Gene—*Bacillus licheniformis* chromosomal DNA was isolated by the spooling method (Sambrook et al., Molecular Cloning: A Laboratory Manual, Cold Spring Harbor Laboratory, Cold Spring Harbor, N.Y. (1989); Dubnau et al., *J. Mol. Biol.* 56, 209 (1971)). Isolated DNA was partially cleaved with EcoRI and BamHI and ligated into the EcoRI and the BamHI sites of pBR322. The ampicillin-resistant colonies were toothpicked onto an LB agar plate containing 1% soluble starch and 50 mg/liter of ampicillin. Five milliliters of LB medium containing 3 mg of D-dycloserine and 0.6% agar was overlaid to each plate After overnight incubation at 37° C., amylase-producing colonies were detected by the addition of 2.5% Lugol's iodine solution. Positive colonies showed in a clear zone around the colony on the agar plates. From these colonies plasmid DNA was isolated by the rapid alkaline extraction method of Sambrook et al. Manipulation of the plasmid of DNA was also carried out by the procedure of Sambrook et al.

Purification of BLMA from *Escherichia coli*—*E. coli* Transformants containing the BLMA gene of *B. licheniformis* were cultured in 2.5 liters of LB medium containing 50 mg/liter of ampicillin at 37° C. for 12–13 h in a jar fermenter and harvested by centrifugation at 10,000×g. The cells were resuspended in 30 ml of 50 mM Tris-HCl buffer (pH 7.5) and sonicated for 5 min in an ice bath. The cell debris was removed by centrifugation at 15,000×g, and the supernatant was fractionated with solid ammonium sulfate at 4° C. The precipitate at 70% saturation of ammonium sulfate was collected by centrifugation and dissolved in 30 ml of 50 mM Tris buffer (pH 7.5) containing 1% of streptomycin sulfate. After centrifugation the supernatant was dialyzed at 4° C. against the same buffer without streptomycin. The dialysate was applied to Sephadex G-100 (3×80-cm) and fractionated with 50 mM Tris-Hcl buffer (pH 7.5). The collected active fractions were concentrated through PM-10 membrane (Amicon Co.) under a nitrogen atmosphere. The concentrate was applied onto a DEAE-cellulose column (3×30-cm) equilibrated with 50 mM Tris buffer (pH 7.5). The column was washed with 250 ml of the same buffer (30 ml/h), and then the enzyme was eluted with a linear gradient of potassium chloride from 0 to 0.8M in the same buffer. The active fractions were eluted at 0.4M NaCl, and the pooled fraction was purified further by a fast protein liquid chromatography (FPLC) system (Pharmacia LKB Biotechnology AB) under the following conditions: column, Mono Q HR 5/5 anion exchanger; buffer A, 20 mM Tris-HCl (pH 7.0); buffer B, 0.5M NaCl in buffer A; 0–100% gradient in 40 min; flow rate, 1.0 ml/min. Fractions with the BLMA activity were eluted at 0.4M NaCl and used to characterize BLMA.

Determination of Molecular Weight and Isoelectric Point—Molecular weight of purified BLMA was determined by SDS-PAGE using 4% stacking and 12% resolving gels of 1-mm thickness as described by Laemmli (*Nature*, 227, 680–685 (1970)). The relative molecular weight of the purified enzyme was estimated by comparing its relative mobility with those of the following reference proteins: β-galactosidase ($M_r$ 116,000), bovine serum albumin (67,000), ovalbumin (43,000), carbonic anhydrase ($M_r$ 30,000), and α-lactalbumin ($M_r$ 15,000). The isoelectric point of the enzyme was estimated on a Phast Gel IEF 4–6.5 using the Phast System (Pharmacia). The isoelectric point of the enzyme was estimated by comparing the relative migration distance of the band.

Enzyme Assay—Hydrolytic activity of BLMA was assayed as described by Suzuki et al. with minor modifications. The mixture containing 0.5 ml of 1% soluble starch (or pullulan, or β-cyclodextrin), 0.25 ml of 0.04M Tris-malate buffer (pH 6.8), and 5 mM of EDTA was prewarmed at 50° C. for 5 min. The enzyme solution of 0.25 ml was added to the prewarmed solution and incubated at 50° C. for 30 min. The reaction was terminated by adding 3 ml of dinitrosalicylate solution (Miller, G. L. *Anal. Chem.*, 31, 426 (1959)). After boiling for 5 min in a water bath, absorbance was measured at 550 nm. One unit of the enzyme was defined as the amount of the enzyme giving an increase of 1.0 absorbance for 30 min under the described conditions.

Action Pattern of BLMA—To determine the hydrolytic action mode, 20 μl of the purified enzyme from the Bacillus donor strain or from the *E. coli* transformant was incubated at 50° C. with 0.5 ml of 1% starch, pullulan, or cyclodextrin solution and 0.25 ml of 0.04M maleate buffer (pH 6.8) containing 5 mM EDTA for 12 h. For the transferring activity test, 1% solution of maltose, maltotriose, maltotetraose, maltopentaose, or maltohexaose was digested with BLMA. For the panosyl transferring activity, 1% pullulan solution was incubated in the presence of 9-, 18-, 27-, 36-, 45-, 54-, and 63% glucose under the same conditions as the above. The reaction mixture was analyzed by TLC, paper electrophoresis, and/or HPLC.

Thin Layer Chromatography and Paper Electrophoresis—TLC was carried out on a Kiesel Gel-60 plate (Merck Co., Ltd.) with a solvent system of isopropyl alcohol/ethylacetate/water (3:1:1, v/v/v). After 5 h of development, the TLC plate was dried and visualized by spraying with 50% sulfuric acid in methanol followed by heating at 110° C. Paper electrophoresis was carried out on Whatman No. 1 paper (20×20-cm) in 0.05M borate buffer (pH 10.0) at 500 V, 2 mA/cm for 1 h (Frahn et al., *Aust. J. Chem.* 12, 65 (1959)). After electrophoresis the paper was dried and sprayed with silver nitrate solution (0.1 ml of saturated silver nitrate+20 ml of acetone). Then 4.5% pentaerythritol ethanolic solution in 0.5M NaOH was sprayed.

High Performance Liquid Chromatography—The chromatographic analysis of the hydrolysates was carried out under the following conditions: column, Machery & Nagel Nucleosil $10NH_2$ (4.6×300 mm); detector, Pye Unicam PU4023 refractive index detector; solvent, acetonitrile/water (65–70:35–30, v/v); flow rate, 1.0 ml/min; sample loop, 20 μl. Before injection, an equal volume of cold acetonitrile was added to the hydrolysate, mixed, and centrifuged. The supernatant was filtered through a membrane filter (0.45 μm), and the filtrate was applied to the injection port.

$^{13}C$ NMR Spectroscopy—The trisaccharide product from the pullulan hydrolysate by BLMA was purified by TLC. $^{13}C$ NMR spectra of the purified trisaccharide and standard panose in $D_2O$ were recorded at 775 MHz (Bruker), in which the signal of internal standard ($CH_3OD$) was at δ50.4.

RESULTS

Isolation of a Gene for BLMA—To isolate a gene encoding maltogenic amylase from *B. licheniformis*, chromosomal DNA was partially double-digested with EcoRI and BamHI, ligated into pBR322, and transformed into *E. coli* HB101. About 600 ampicillin-resistant colonies were screened for the maltogenic amylase gene, and one positive colony was selected by its amylolytic activity upon D-cycloserine treatment. Other amylolytic clones including α-amylase showed starch-hydrolyzing activity within D-cycloserine treatment of the transformed *E. coli* cells. Plasmid DNA, pIJ322, was isolated from the amylase-positive colony, and the insert size in the recombinant plasmid was 3.5 kbp. It was confirmed by retransformation of *E. coli* HB101 with pIJ322. The control transformant carrying pBR322 did not show any amylolytic activity upon D-cycloserine treatment.

Figure 1B:
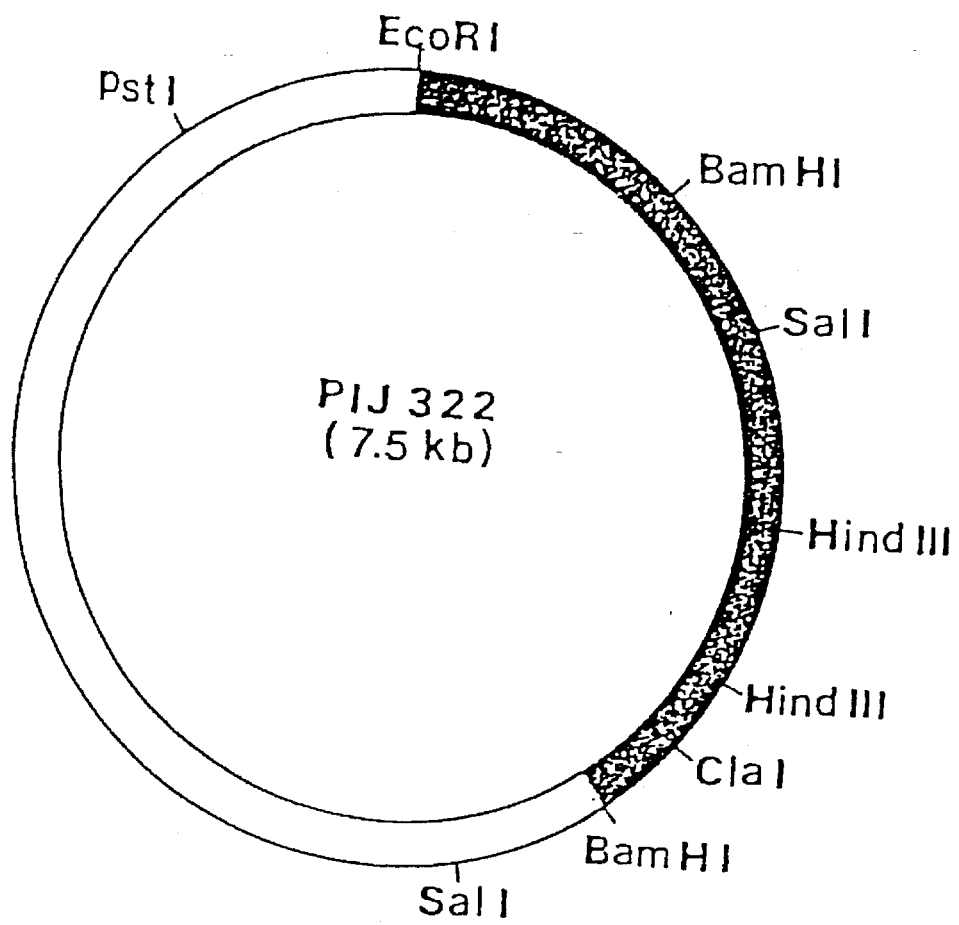
FIG. 1B.—Partial restriction enzyme map of the recombinant plasmid pIJ322. Open region is the vector DNA pBR322 and closed region is the insert containing the gene encoding BLMA map.

To analyze the genomic DNA structure of the gene encoding BLMA in *B. licheniformis*, genomic Southern blotting analysis was carried out. One EcoRI fragment of 6 kbp and two BamHI fragments of 2.5 and 2.3 kbp were hybridized to pIJ322 labelled with [α-32p] dATP (FIG. 1A). This result was consistent with the presence of the internal BamHI site on the pIJ322 insert. Double digest of the genomic DNA with EcoRI and BamHI had 2 DNA fragments hydridized to the probe, pIJ322 (FIG. 1A; lane D). The sizes of the two DNA fragments were identical to those of pIJ322 digested with EcoRI and BamHI (FIG. 1A; lane E). This indicated that the DNA fragment of *B. licheniformis* containing the BLMA gene was cloned in *E. coli* without apparent rearrangement. As shown in the partial restriction endonuclease map of pIJ322, the insert has a single restriction endonuclease site for EcoRI, BamHI, ClaI, and SalI, and two for HindIII (FIG. 1B). Comparing the intensity of the plasmid pIJ322 insert reconstructed with the equivalent amount of a single copy gene, the intensity of bands suggest that there is only a single copy of BLMA gene in *B. licheniformis* (data not shown). A simple genomic restriction fragment pattern also supports a unique gene structure.

Figures 3A, 3B:
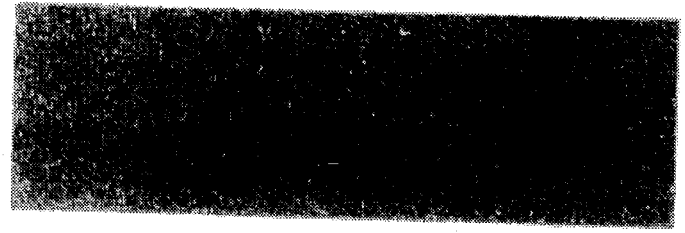
FIG. 3A.—Electrophoresis of purified BLMA. 12.5% SDS-PAGE was carried out by Phast System and stained with Coomassie Blue. Lane M, molecular weight marker; lane B, purified BLMA.
FIG. 3B.—Electrofocusing gel. Electrofocusing was carried out on a Phast Gel IEF 4–6.5. Separated Proteins were visualized by silver staining.

Structural Analysis of the BLMA Gene—To analyze the structure of the BLMA gene, nucleotide sequencing was carried out by Sanger's chain termination method (FIG. 2). There was one open reading frame encompassing 1740 nucleotides encoding a protein of 580 amino acids. The molecular size of the deduced polypeptide was calculated to be 66,931 daltons which is consistent with the apparent molecular weight of BLMA, 64,000 daltons, estimated by SDS-PAGE (FIG. 3A). The insert of the clone contained about 291 bp and 1.2 kbp of 5'- and 3'-flanking sequences, respectively. Putative promoter elements, TTAACA (−35 element) and TAATTT (−10 element), are present around 93 nucleotide and 54 nucleotide upstream of the translational initiation site, respectively. A putative Shine-Dalgarno sequence, AGGGGG, was also noticed around 8 nucleotide upstream of the putative translation initiation site. These results are quite consistent with the functional analysis of pIJ322 by serial deletion.

Purification and Characterization of BLMA—To study the reaction mechanism of BLMA, the enzyme produced by the transformed *E. coli* was purified to an apparent homogeneity by using fast protein liquid chromatography (Kim, J. R., M. S. thesis, Seoul National University Press, Seoul, Korea (1991)). The purified fraction did not contain any detectable amount of contaminating proteins as judged by SDS-PAGE and electrofocusing (FIG. 3). The molecular weight of BLMA was determined to be about 64,000 daltons by SDS-PAGE, and the isoelectric point of the enzyme was found to be around pH 5.4. The optimum pH of hydrolyzing activity was pH 6 for pullulan, pH7 for starch, but around pH 7–9 for cyclodextrin.

Figure 4A:
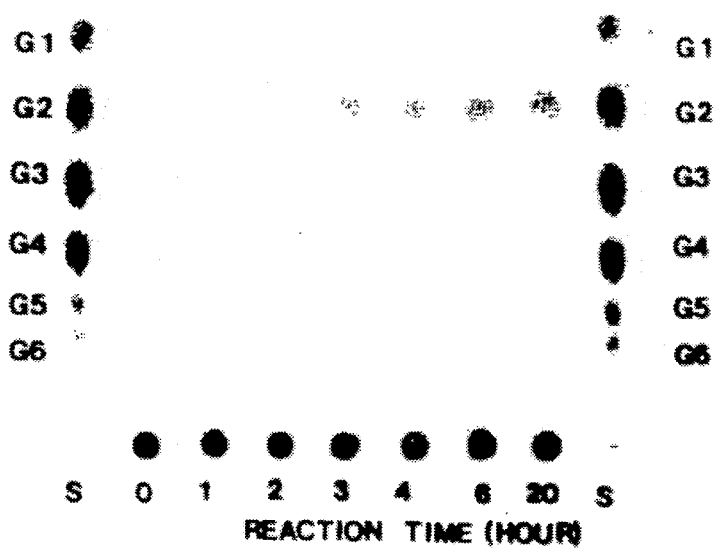
FIGS. 4A–4C.—Thin layer chromatograms of the hydrolysis products from various substrates by BLMA. Soluble starch (FIG. 4A), β-cyclodextrin (FIG. 4B), and pullulan (FIG. 4C) were incubated with the purified enzyme, and the reaction products were taken at various time points and analyzed by TLC using isopropyl alcohol/ethylacetate/water (3:1:1, v/v/v) as solvent. G1, G2, G3, G4, G5, and G6 are standards of glucose, maltose, maltotriose, maltotetraose, maltopentaose, and maltohexaose, respectively.
Figure 4B:
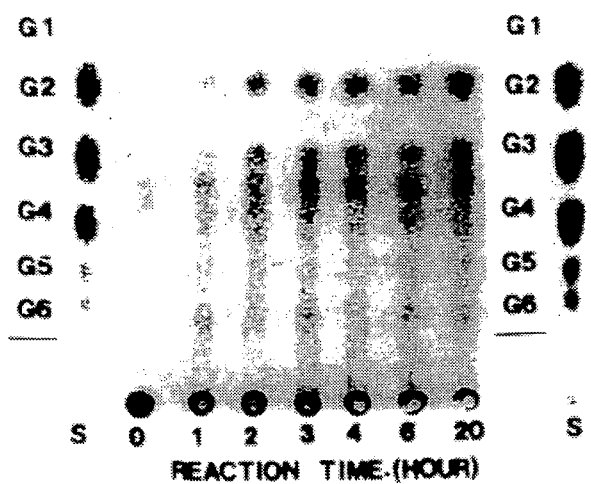
Figure 4C:
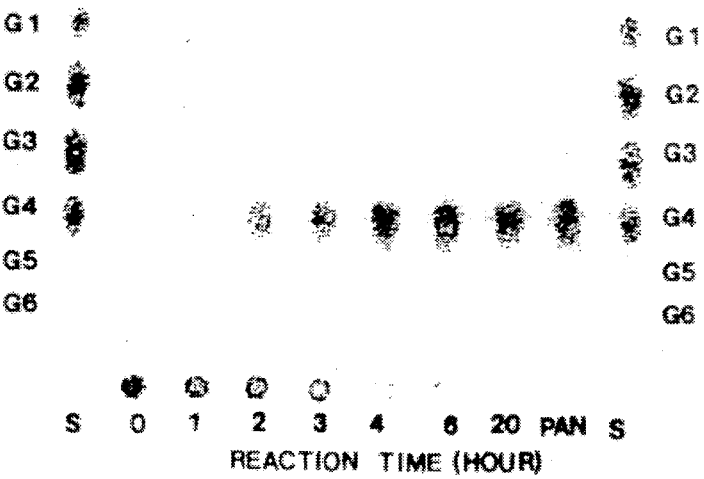

Hydrolytic Activity of BLMA—To test the substrate specificity of BLMA, several different substrates were subjected to hydrolysis by BLMA. The substrate specificity of BLMA was compared with that of BLTA. Soluble starch, pullulan, and cyclodextrin were readily hydrolyzed by BLMA, while BLTA hydrolyzed only soluble starch. To examine the hydrolysis pattern of BLMA, the reaction product was analyzed by TLC at various time points of reaction as shown in FIG. 4. The major product at various stages of soluble starch hydrolysis was apparently maltose (FIG. 4A). As the reaction proceeded, the quantity of maltose increased. When β-cyclodextrin was used as the substrate, the enzyme liberated low molecular weight oligosaccharides, in which the main product was maltose (FIG. 4B). In case of pullulan, which contains one α-1,6- and two α-1,4-glycosidic linkages alternately, the major reaction product migrates at the position between maltotriose and maltotetraose (FIG. 4C). Comparison of this product with the panose standard suggested that it could be panose.

Figure 6:
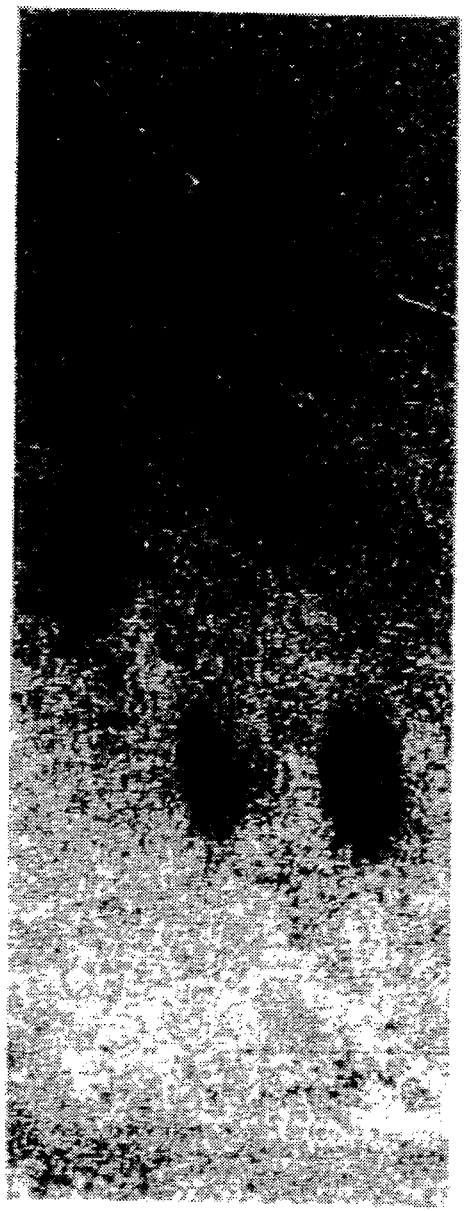
FIG. 6.—Paper electrophoresis to identify the panose and isopanose. IP, isopanose standard; P, panose standard; H, hydrolysis product of pullulan by BLMA FIG. 7.—High performance liquid chromatogram of the pullulan hydrolysis products by BLMA in the presence of 20% glucose. Position of standard glucose (1), maltose (2), maltotriose (3), maltotetraose (4), and maltopentaose (5) are indicated by arrows. P, panose; R, Glcpαl-6Glcpαl-4Glcpαl-4Glc added as internal reference; U, unknown branched tetrasaccharide assumed to be Glcpαl-6Glcpαl-4Glcpαl-6Glc. The HPLC analysis was carried out under the following conditions: column, Machery & Nagel Nucleosil 10NH$_2$ (4.6×300 mm); detector, Pye Unicam PU4023 refractive index detector; solvent, acetonitrile/water (75:25, v/v); flow rate, 1.0 ml/min; sample loop, 20 μl.

The result of TLC analysis for pullulan hydrolysis was consistent with that of HPLC analysis (FIG. 5). The major hydrolysis product from pullulan treated with BLMA showed the same retention time as panose in HPLC (FIG. 5B). Panose and isopanose, however, were not distinctively separated by TLC and HPLC under these conditions. Therefore, paper electrophoresis was carried out to identify this major product. FIG. 6 clearly shows that the hydrolysis product from pullulan treated with BLMA was panose, rather than isopanose.

The hydrolysis product of pullulan by BLMA was analyzed further by $^{13}$C NMR after isolation of the major product by TLC. The spectrum of the isolate was shown to be identical to that of the authentic panose (data not shown). These results made it sure that the trisaccharide produced by BLMA was clearly panose.

Figure 10:
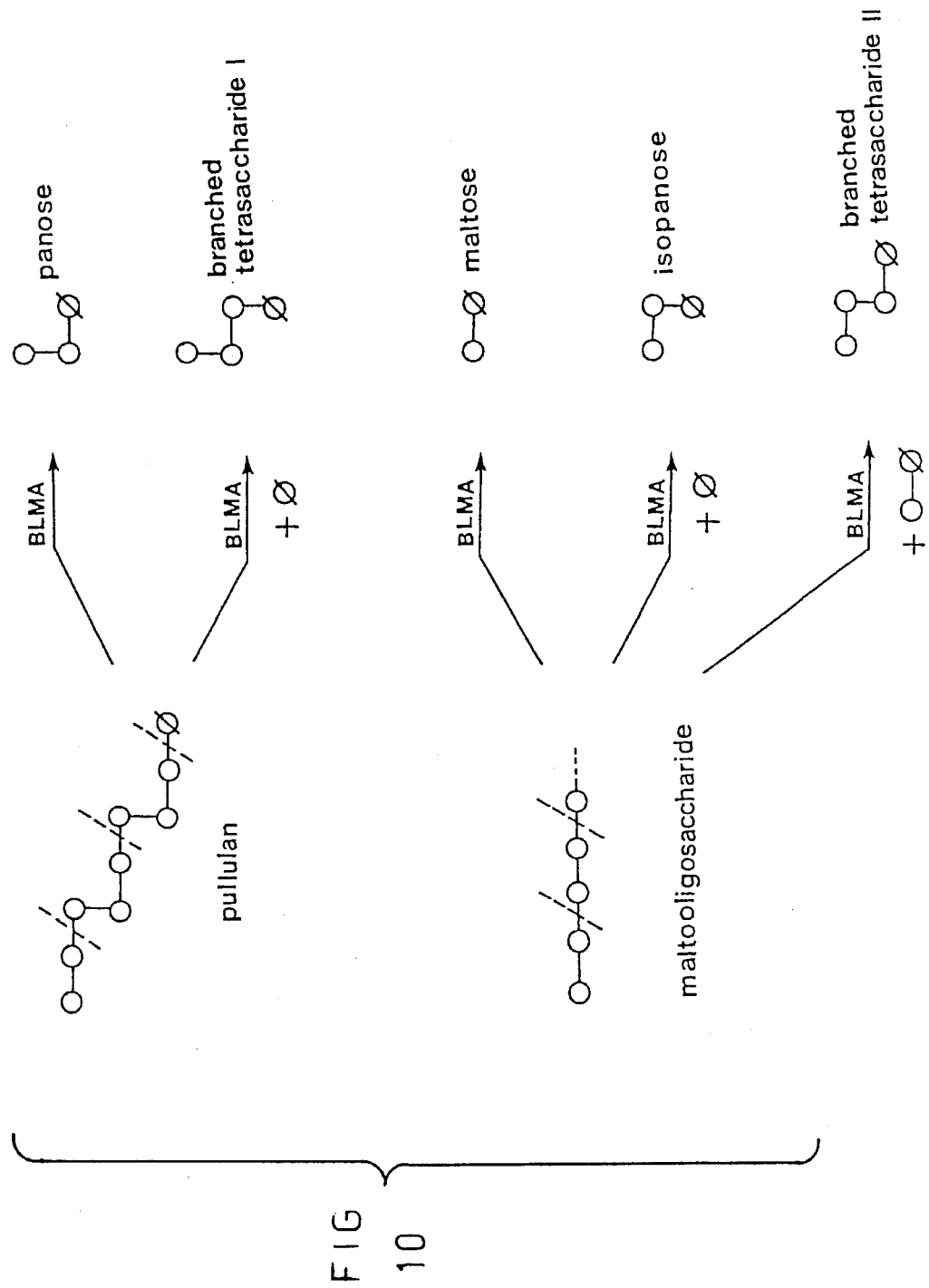
FIG. 10.—Proposed action pattern of BLMA, coupling of hydrolysis, and transferring activity of BLMA generate. Open circles and slashed circles denote non-reducing glucopyranosyl residues and reducing glucose residues, respectively. Horizontal lines and vertical lines connecting circles indicate α-1,4- and α-1,6-glucosidic linkages, respectively. The structure of branched tetrasaccharides I and II are Glcpαl-6Glcpαl-4Glcpαl-6GlC and Glcpαl-4Glcpαl-6Glcpαl-4Glc, respectively.

These results altogether suggested that BLMA hydrolyzed every other α-1,4-glycosidic linkage to produce maltose from soluble starch. It also hydrolyzed the α-1,4-linkage of pullulan with the production of panose, which the usual α-amylase do not carry out. It, however, could not hydrolyze the α-1,4-linkage right next to the α-1,6-linkage (FIG. 10).

Figure 7:
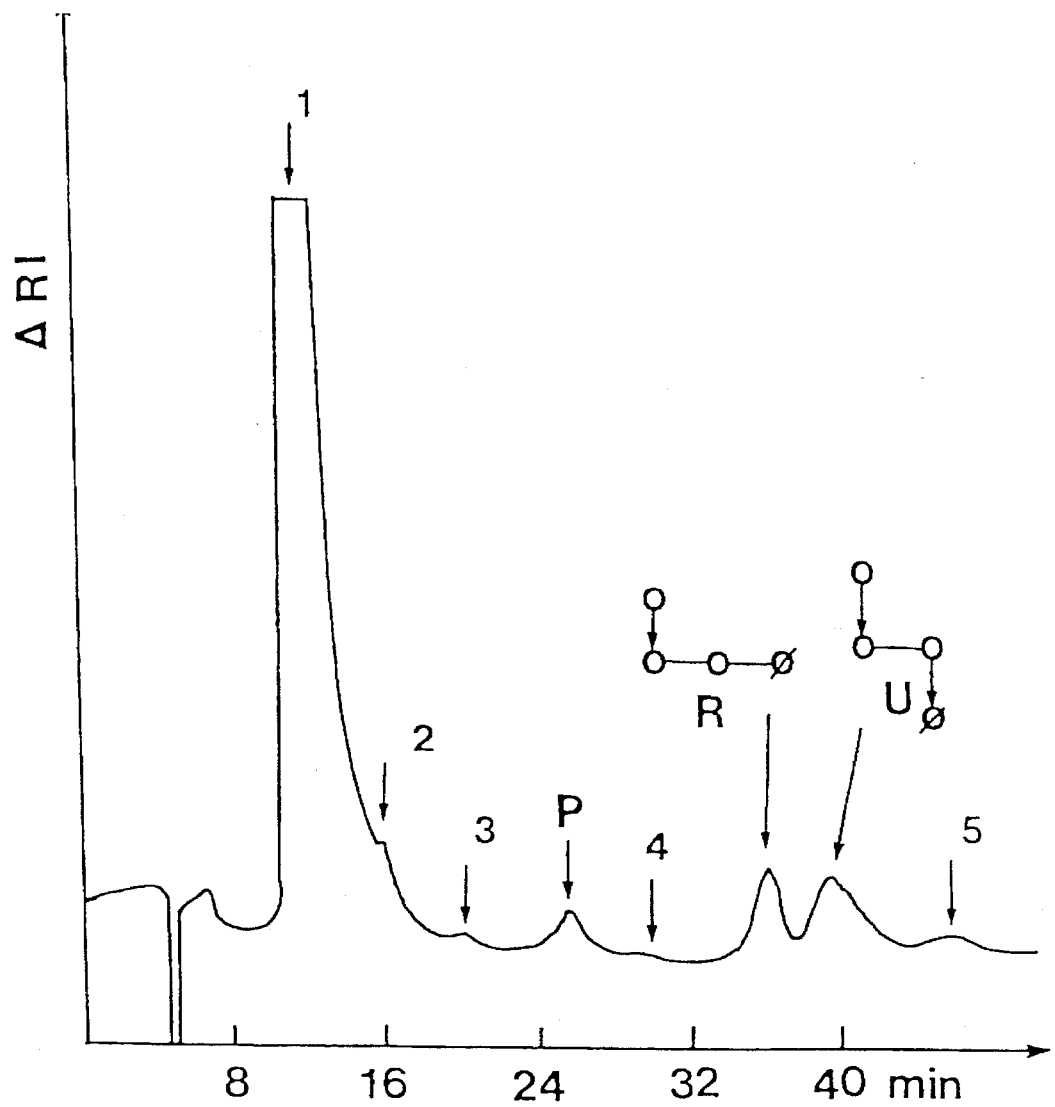

Transferring Activity of BLMA—To examine the transferring activity of the enzyme, pullulan was incubated with BLMA in the presence of a high concentration of glucose, and the reaction products were analyzed by HPLC as shown in FIG. 7. The reaction products were identified as panose, glucose, maltose, and an unknown oligosaccharide which were detected between maltotetraose and maltopentaose. Retention time of the unknown oligosaccharide suggested that it might be a branched tetrasaccharide. It was eluted later than a branched maltotetraoses, Glcpαl-6Glcpαl-4Glcpαl-4Glc, which was added to the reaction product as an internal reference. The unknown branched tetrasaccharide was considered to be Glcpαl-6Glcpαl-4Glcpαl-6Glc, which was produced by the transferase activity of BLMA.

Figure 8:
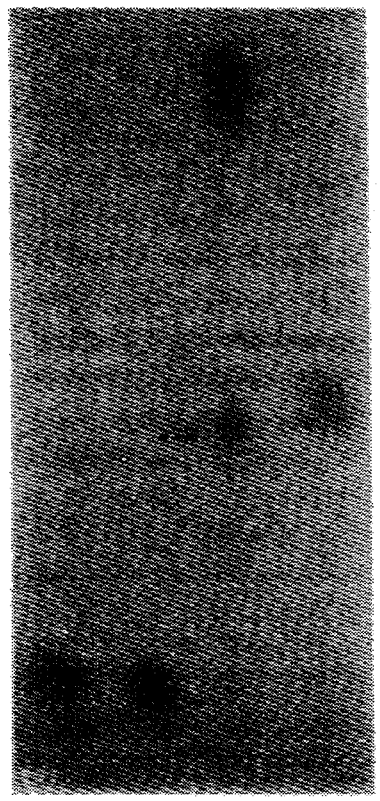
FIG. 8.—Paper electrophoresis to identify panose and isopanose. G3, maltotriose; P, panose: T, maltotriose+glucose+BLMA; IP, isopanose. The fast migrating spot in lane T was identified as glucose.

Specificity of the transferring activity of BLMA was demonstrated further by digesting maltooligosaccharide. Maltotriose was degraded by BLMA in the presence of glucose to form a product with the migration distance corresponding to that of isopanose as shown in FIG. 8. This result suggested that the bond formed by the transferring activity of BLMA was α-1,6linkage between the reducing end of maltose and C-6 of acceptor glucose. These results strongly suggested that the unknown branched tetrasaccharide generated from pullulan in the presence of glucose might be Glcpαl-6Glcpαl-4Glcpαl-6Glc (FIG. 7).

Figure 9:
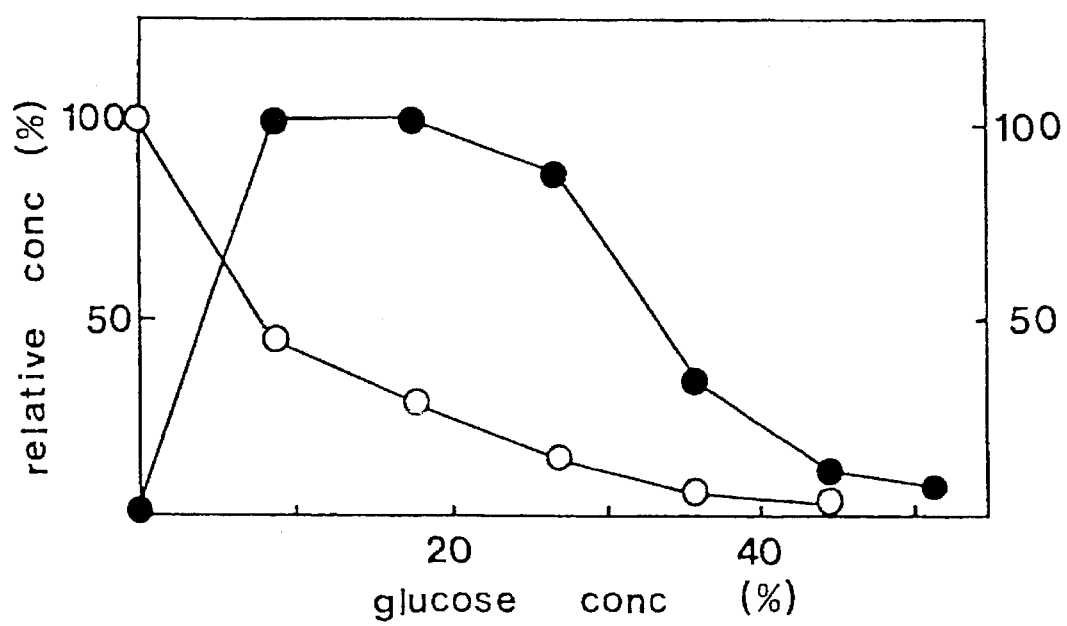
FIG. 9.—Effects of glucose concentration on the transferring activity of BLMA. Open circles denote panose and closed circles denote the branched oligotetrasaccharide concentration in the reaction mixture.

The effect of glucose concentration on the formation of branched tetrasaccharide was tested by digesting pullulan in various concentrations of glucose (FIG. 9). Formation of the branched tetrasaccharide was maximum at the concentration of 10–27% glucose, while at the concentration of 36% glucose the formation of the branched tetrasaccharide was dramatically decreased. The branched tetrasaccharide was not formed in the presence of over 45% glucose in the reaction mixture. The concentration of the branched tetrasaccharide increased with the increase of incubation time. These results indicated that in the presence of glucose pullulan was degraded to panose which was subsequently transferred to C-6 of glucose by hydrolyzing and transferring activities of BLMA. In this process, glucose served as an acceptor for panose, and, therefore, the concentration of panose was kept relatively low for the formation of branched tetrasaccharide during the coupling reactions. BLMA, however, did not catalyze the formation of branched tetrasaccharide from the mixture of panose and glucose, suggesting the coupling of hydrolysis and transferring reactions (data not shown).

DISCUSSION

The well-known α-amylase produced by *Bacillus licheniformis*, BLTA, was analyzed to be extremely thermostable (rf. Tuuki et. al., 1986 Kim PhD Thesis). The enzyme hydrolyzes starch into mostly maltohexaose and maltoheptaose but does not degrade pullulan, α- and β-cyclodextrin. However, the novel maltogenic amylase of the present invention is not thermostable. The optimum temperature for BLMA activity was determined to be around 50° C. D-value of BMLA at 50° C., 55° C., and 60° C. was 40.5 min, 20.5 min, and 3.3 min, respectively. The molecular weight of BLMA ($M_r$ 64,000 daltons) differs from that of BLTA ($M_r$ 55,200 daltons). In contrast to BLTA which hydrolyzes starch only, BLMA hydrolyzes soluble starch, α-, and β-cyclodextrin to maltose. BLMA is also capable of hydrolyzing pullulan to panose.

Campbell (*Arch. Biochem. Biophys.* 54, 154 (1955)) and Bliesmer and Hartman (*J. Bacteriol.*, 113, 526 (1973)) have reported that two different amylase genes might exist in Bacillus sp. because two different α-amylases were produced at different culture temperatures. BLMA could be produced by one of the two amylase genes which was barely expressed in *B. licheniformis*. The result of southern analysis of *B. licheniformis* genomic DNA digests using pIJ322 as the probe indicated that the gene encoding the thermostable α-amylase were not homologous to the BLMA gene. No other hand than those coresponding to the regions of the BLMA gene was hybridized. The activity of BLMA was not detectable in the culture broth of the original *B. licheniformis* strain but barely detected in cell lysate prepared from the culture at very late growth phase. A fairly high level of the enzyme activity, however, was obtained in *E. coli* transformed with the BLMA gene, which might result from regulated gene expression and increased gene dosage by cloning the gene on multi-copy plasmid.

When the deduced amino acid sequence of BLMA was compared with those of various amylases reported, limited similarities at four prominently conserved regions were noticed (Table 1). A relatively high similarity was noticed at mal-conserved region I which was considered to be the calcium-binding domain of amylase (Kuriki et al., *J. Gen. Microbiol.* 135, 1521 (1989) (II)). The various spacings between these conserved domains could reflect the chemical nature of the reaction catalyzed and thus the final product formed by the enzyme.

Most of the amylogytic enzymes isolated so far are known to be secreted to the periplasmic space or into the culture medium. The amino acid sequence deduced from the nucleotide sequence indicated that the BLMA enzyme is not likely to be secreted to other cell compartments. This was well supported by the result of the localization of BLMA produced in *E. coli*. All of the enzyme was localized in the cytoplasmic space of the *E. coli* cells.

Even though the substrate specificity of BLMA from the clone seemed to be similar to that of α-amylase II from *B. thermoamyloliquefaciens* KP1071, α-amylase from *T. vulgaris* R-49, maltogenic α-amylase from *B. megaterium* (Hebeda et al., Starch 40, 33 (1988)), pullulanase from *Klebsiella aerogenes* (Bender et al., *Biochem. Z.*, 334, 79 (1961)), isopullulanase from *Aspergillus niger* (Sakano et al., *Agric. Biol. Chem.*, 35, 971 (1971) (II)), and neopullulanase from *B. stearothermophilus* (Suzuki et al., *Appl. Microbiol. Biotechnol.*, 21, 20 (1985) (III), the chemical nature of the reaction catalyzed by BLMA was different from theirs. BLMA could attack typically every other endo α-1,4-linkages but not α-1,6-linkage. It, however, could not hydrolyze the α-1,4-linkage next to the α-1,6-linkage, which resulted in the release of panose exclusively from pullulan rather than isopanose. Pullulanase, however, produced isopanose rather than panose. Neopullulanase from *B. stearothermophilus* could hydrolyze α-1,6-linkage as well as α-1,4-linkage and, therefore, released a significant amount of glucose and maltose in addition to panose. The substrate specificities of various unusual amylases are summarized in Table II.

It is interesting to note that BLMA had transferring activity in addition to hydrolyzing activity. A branched tetrasaccharide (Glcpαl-6Glcpαl-4Glcpαl-6Glc) having a new α-1,6linkage was formed as BLMA degraded pullulan in the presence of glucose. Hydrolysis specificity of α-amylase from *B. megaterium* and *T. vulgaris* seemed to be quite similar to that of BLMA. David et al., however, pointed out that the hydrolysis reaction of α-amylase from *B. megaterium* in the presence of glucose was gradually replaced by the coupling reaction with the formation of Glcpαl-6Glcpαl-4Glcpαl-4Glc which was formed by transfer of panose from pullulan to the C-4 position of the glucose molecule rather than the C-6 position. $^1$H and $^{13}$C NMR studies confirmed that it did catalyze the formation of α-1,4-linkage during the transfer reaction. In contrast, BLMA catalyzed the formation of α-1,6-linkage during the transfer reaction (Table II).

The transfer reaction by BLMA in the presence of maltotriose and glucose gave isopanose in which α-1,6-linkage was formed by the maltosyl transfer. Incubation of maltotriose and maltose with BLMA also resulted in the formation of a branched maltotetraose in which two maltose units are linked by a α-1,6-linkage. In the meantime, when pullulan was incubated with BLMA in the presence of glucose, another branched maltotetraose was produced. The retention time of the branched maltotetraose differed from those of maltotetraose and Glcpαl-6Glcpαl-4Glcpαl-4Glc, indicating the existence of α-1,6-linkage in the tetraose. The retention time of the unknown products on the HPLC column was between those of linear maltotetraose and maltopentaose suggesting the existence of maltotetraose with a α-1,6-linkage which did not exist in the initial reaction mixture. From the results, the action pattern of BLMA can be summarized as in FIG. 10.

Combinations of donors such as maltose or panose and acceptor molecules such as glucose or maltose in the presence of BLMA would give rise to a variety of branched oligosaccharides. Such a novel transferring activity of BLMA could be utilized to synthesize various kinds of branched oligosaccharides.

From the foregoing, it will now be apparent that the present invention has provided an *Escherichia coli* containing a gene *Bacillus licheniformis* (BLMA) which has the ability to hydrolyze cyclodextrin, pullulan, as well as starch. This *Escherichia coli* was deposited with the American Type Culture Collection (ATCC), 12301 Parklawn Drive, Rockville, Md., 20852, U.S.A. on Mar. 7, 1990 and received accession number ATCC 68319. The novel maltogenic amylase of the present invention has sugar transferase activity in the presence of glucose with the formation of α-1,6-linkage. Therefore, the BLMA enzyme is useful in manufacturing a mixture of branched oligosaccharides.

Although the invention has been shown and described in respect to certain preferred embodiments, it is obvious that equivalent alterations and modifications will occur to others skilled in the art upon the reading and understanding of the specification. The present invention includes all such equivalents and modifications, and is limited only by the scope of the claims.

What is claimed is:

1. An *Escherichia coli* containing a gene coding for a maltogenic amylase of *Bacillus licheniformis* (BLMA) which is ATCC 68319, wherein said gene has a length of about 3.5 kb; said gene expresses a gene product capable of hydrolyzing cyclodextrin, pullulan, as well as starch at an optimum temperature of about 50° C. at a pH of about 7; said gene product has sugar transferase activity in the presence of glucose; and said *Escherichia coli* produces said gene product optimally when grown in Luria broth, for 24 hours, at 37° C.

2. The isolated maltogenic amylase (BLMA) produced by the *Escherichia coli* of claim 1.

* * * * *